(12) United States Patent
Tsuchiya

(10) Patent No.: US 8,822,204 B2
(45) Date of Patent: Sep. 2, 2014

(54) CULTURE APPARATUS FOR MICROSCOPE VIEWING AND METHOD THEREFOR

(75) Inventor: Hideharu Tsuchiya, Fujinomiya (JP)

(73) Assignee: Tokai Hit Co., Ltd., Fujinomiya-shi (JP)

( * ) Notice: Subject to any disclaimer, the term of this patent is extended or adjusted under 35 U.S.C. 154(b) by 0 days.

(21) Appl. No.: 13/808,004

(22) PCT Filed: Mar. 22, 2011

(86) PCT No.: PCT/JP2011/001660
§ 371 (c)(1),
(2), (4) Date: Jan. 2, 2013

(87) PCT Pub. No.: WO2012/127523
PCT Pub. Date: Sep. 27, 2012

(65) Prior Publication Data
US 2013/0109081 A1 May 2, 2013

(51) Int. Cl.
| | |
|---|---|
| C12M 1/38 | (2006.01) |
| C12M 1/34 | (2006.01) |
| G02B 21/30 | (2006.01) |
| C12M 1/00 | (2006.01) |
| G02B 7/00 | (2006.01) |
| C12M 1/32 | (2006.01) |
| G02B 21/34 | (2006.01) |

(52) U.S. Cl.
CPC .............. C12M 41/14 (2013.01); C12M 41/36 (2013.01); G02B 7/008 (2013.01); C12M 23/12 (2013.01); G02B 21/34 (2013.01); G02B 21/30 (2013.01)
USPC ................. 435/286.1; 435/288.4; 435/288.7; 435/303.1; 359/395; 359/398

(58) Field of Classification Search
CPC ...... C12M 23/12; C12M 41/14; C12M 41/36; G02B 7/008; G02B 21/30
USPC ......... 435/288.7, 288.4, 303.1, 809; 359/395, 359/398
See application file for complete search history.

(56) References Cited

U.S. PATENT DOCUMENTS 4,629,862 A * 12/1986 Kitagawa et al. ............. 219/200
(Continued)

FOREIGN PATENT DOCUMENTS

| JP | A-2004-141143 | 5/2004 |
|---|---|---|
| JP | A-2007-108445 | 4/2007 |
| JP | A-2008-259430 | 10/2008 |

OTHER PUBLICATIONS

Jun. 14, 2011 Written Opinion of the International Searching Authority issued in International Application No. PCT/JP2011/001660 (with partial translation).
(Continued)

*Primary Examiner* — William H Beisner
(74) *Attorney, Agent, or Firm* — Oliff PLC

(57) ABSTRACT

A culture apparatus for microscopic viewing enables effective microscopic viewing at high magnification of samples such as cells suspended in a culture solution while the samples are maintained at a uniform temperature. The apparatus is used to microscopically view a sample placed on a microscope stage, and is provided with a housing unit that houses the vessel containing a culture solution and the sample; a lid that closes the aperture on the upper surface side of the housing unit; a transparent sheet top heater provided in the portion of the lid that corresponds to the viewing area; and a temperature detecting means where a thin wire detection unit penetrates into the interiors of the housing unit and a well plate to directly measure the temperature of the culture solution. Based on the temperature information, a controller controls the temperature of the transparent sheet top heater using a feedback method.

18 Claims, 7 Drawing Sheets

(56) References Cited

U.S. PATENT DOCUMENTS

2005/0248836 A1 11/2005 Tsuchiya
2007/0291354 A1* 12/2007 Harada .................. 359/395
2009/0141345 A1 6/2009 Tsuchiya

OTHER PUBLICATIONS

Examining Authority issued in International Application No. PCT/JP2011/001660 (with partial translation).

Jun. 26, 2012 Written Opinion of the International Preliminary Aug. 22, 2012 International Preliminary Report on Patentability issued in International Application No. PCT/JP2011/001660 (with partial translation).

Jun. 14, 2011 International Search Report issued in International Application No. PCT/JP2011/001660 (with translation).

* cited by examiner

CULTURE APPARATUS FOR MICROSCOPE VIEWING AND METHOD THEREFOR

FIELD OF THE INVENTION

The present invention relates generally to a culture apparatus for microscope viewing suitable for the observation of specimen such as cells.

BACKGROUND OF THE INVENTION

Culture apparatus for microscope viewing of this type such as those described in Japanese Patent Laid-open (kokai) public disclosure 2008-259430 and shown in FIG. 8, are well known in the art. A culture apparatus for microscope viewing 100 shown in FIG. 8 comprises a housing unit 103 and a lid 107 for closing an upper opening of the housing unit. A water tank 105 is provided along the inner side wall of the housing unit 103. The interior space defined by the inner edge of the water tank 105 can accommodate a container such as a well plate W for holding culture media or medium A and a specimen or specimens B. The culture apparatus, which accommodates the well plate, are adapted to be rested on the stage of a microscope.

In order to hold the specimen B such as cells within the culture solution A under the conditions suitable for making observation, it is required to keep a temperature of the culture solution A stable at or around 37° C. In the prior art, a heater plate 109 of thin aluminum sheet of high thermal conductivity is provided over the lower opening of the housing unit 103 for heating the solution A within the well plate.

The heater plate 109 has a plurality of through holes 111 at positions corresponding to wells w of the well plate W for making the wells w remain for the microscope viewing.

Recently, there has been used an inverted microscope for high magnification observation. In order to make observation operation in high magnification, the objective lens R is likely to be close to the lower surface of the housing unit 103. Accordingly, if observation object is changed from one well to an adjacent well, as shown in arrow in the figure, the objective lens R is retracted from the one well, the housing unit 103 is moved in X-Y (two dimensional) directions on the on the microscope stage S in order that the objective lens S faces on the adjacent well, and the objective lens R is closed to the adjacent well, because the wells w is plated on the heater plate 109. This is a cumbersome operation. Even if such operation can be effected automatically, complicated programming is required. Further, if there is used as the well plate, a multi-type one (for example, 96 wells), it is difficult to bring the objective lens R even close to the lower surface of unit 103, because the hole web of the heater plate 108 is smaller.

So called oil or water immersion lens in which the space between the exposed lower surface of the container and the objective lens R is filled with oil or water, is used to observe the specimen B for clear observation in high magnification. However, the liquid ball made on the top of the objective lens R, which fills the space is apt to be broken under the effect of the reciprocal movement of the objective lens R.

On the other hand, when the heater plate 109, instead, has one large though hole, which cover all of the wells w and heats the wells s by w by transferring heat energy from the web of the heater plate 109, it is impossible to heat each well w equally, because of difference in distance between each well and the heater plate. In other words, the one wells w adjacent the web of the heater plate 108 is rich-heated, and the other wells w far away from the web thereof is poor-heated.

TECHNICAL LITERATURE OF PRIOR ART

Patent Literature

Japanese Patent Laid-open (kokai) public disclosure 2008-259430

SUMMARY OF THE INVENTION

Problem or Problems to be Solved by the Invention

The object of the present invention is to provide a culture apparatus for microscope viewing enabling effective microscopic viewing in high magnification a specimen such as cells dispersed in the culture solution, and the method for using the same.

The Means for Solving the Problem or Problems

In accordance with the invention defined as a first aspect, there is provided a culture apparatus for microscope viewing enabling effective microscopic viewing a specimen placed on a stage of the microscope including a housing unit for accommodating a container holding a culture solution including the specimen therein, and a lid for closing an upper opening of the housing unit, with the housing unit having a lower opening of a size into which is removably fit a well plate and no heating plate narrowing the lower opening comprising: a transparent sheet top heater provided over a portion of the lid that corresponds to the viewing area; and a temperature detecting means in which a thin wire detector penetrates into the interior of the housing unit and further is immersed in the culture solution hold in a container to measure the temperature of the culture solution supplied thereto directly; wherein the temperature of the transparent sheet top heater is controlled through a feedback method on the basis of the temperature information obtained from the temperature detecting means.

In accordance with the invention defined as a second aspect, there is provided a culture apparatus for microscope viewing according to the first aspect further comprising: an introducing means for introducing the detector of the temperature detecting means into the housing unit.

In accordance with the invention defined as at third aspect, there is provided a culture apparatus for microscope viewing according to the first or second aspect, further comprising: a dedicated lid for the container; wherein the detector of the temperature detecting means is adapted to be inserted into the container through an introducing means provided on the container.

In accordance with the invention defined as a fourth aspect, there is proved a culture apparatus for microscope viewing according to the third aspect, wherein: the lid for the container is made of a transparent glass material.

In accordance with the invention defined as a fifth aspect, there is provided a culture apparatus for microscope viewing according to any of the first to fourth aspects wherein: within the housing unit is accommodated a container having a plurality of sections or a plurality of containers, the detector of the temperature detecting means being introduced into one of the sections or one of the containers to detect the temperature thereof, and remaining sections or containers being used for the microscopy of the specimen.

Effect to be Obtained from the Invention

In accordance with a culture apparatus for microscope viewing of the present invention, effective microscopic viewing in high magnification the specimen such as cells dispersed in the culture solution kept in the constant temperature is accomplished efficiently.

BRIEF DESCRIPTION OF THE DRAWINGS

Embodiments of the present invention will now be described more fully with reference to the accompanying drawings in which.

DETAILED DESCRIPTION OF THE INVENTION

A culture apparatus 1 for microscope viewing in accordance with an embodiment of the present invention will now be described with reference to FIGS. 1-7.

The culture apparatus 1 includes a housing unit 3 and a lid 53.

The structure of the housing unit 3 will now be described as follows.

Figure 1:
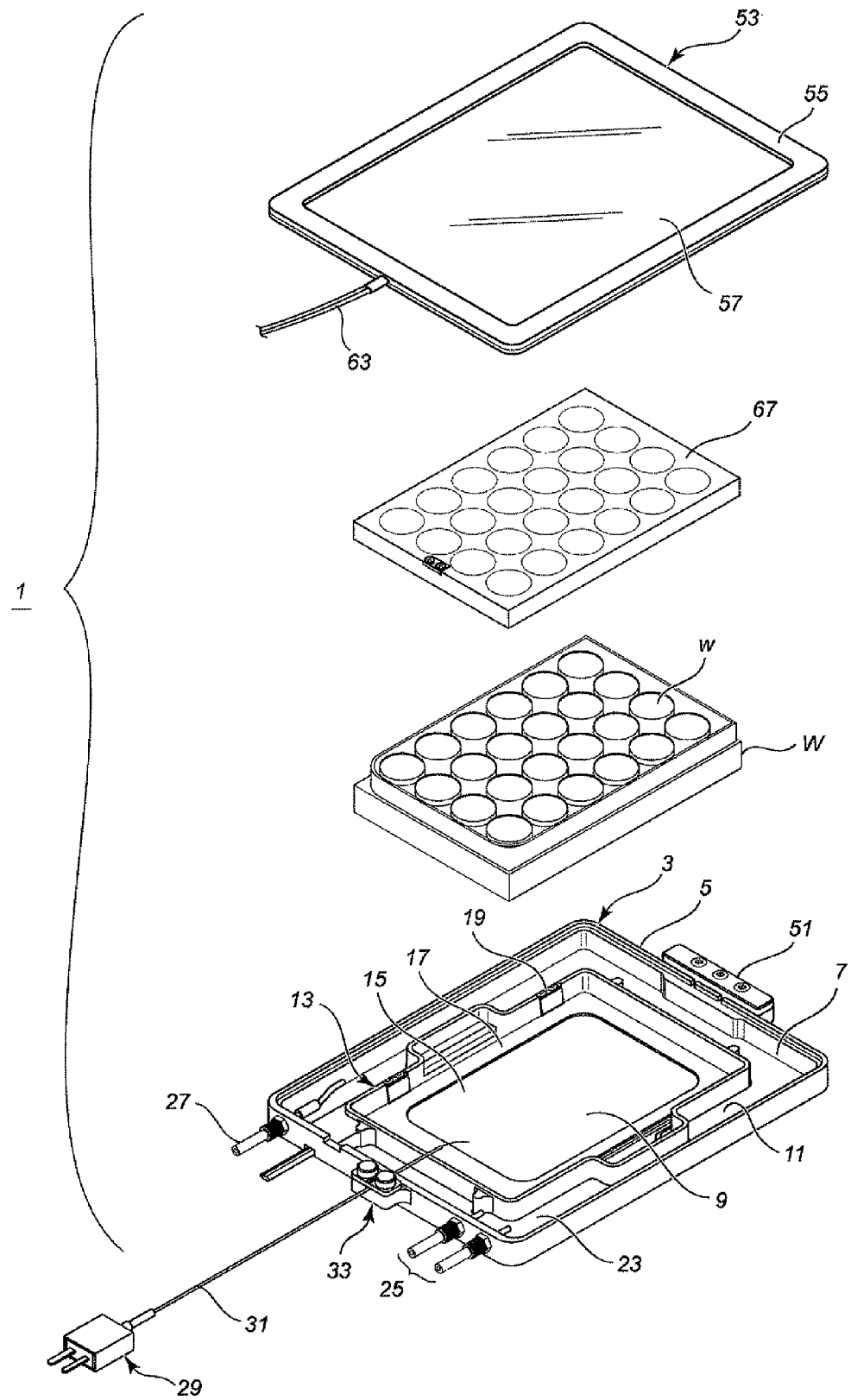
FIG. 1 is an exploded perspective view illustrating an embodiment culture apparatus for microscope viewing according to the present invention.
Figure 2:
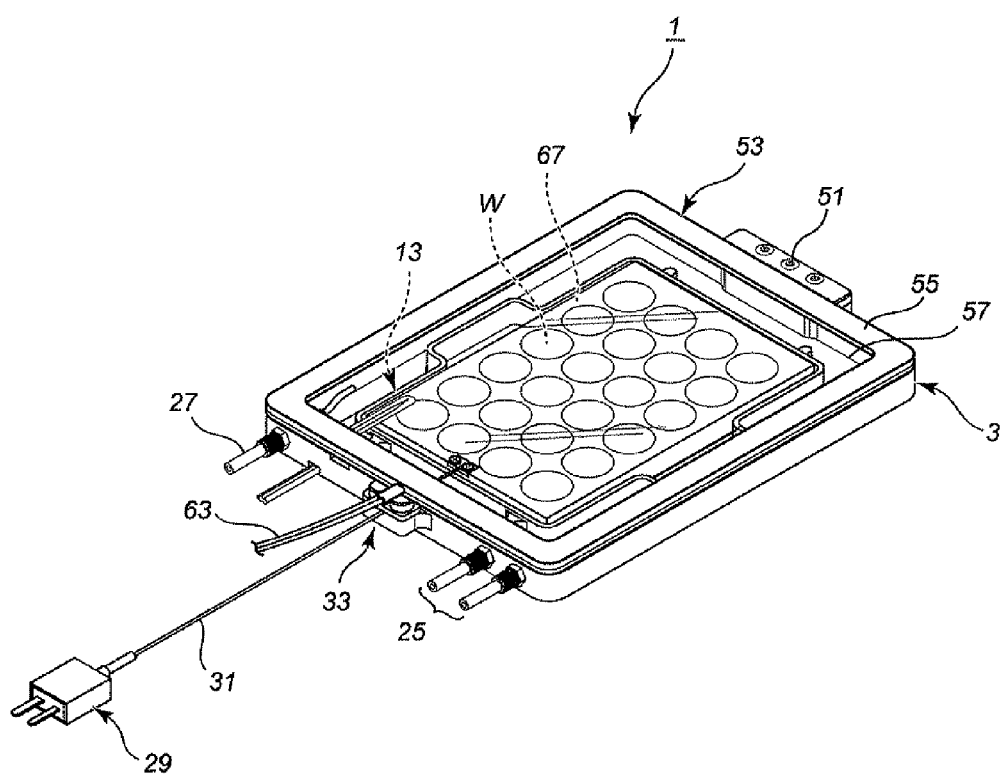
FIG. 2 is a perspective view of the FIG. 1 culture apparatus from seen from the upper side.
Figure 3:
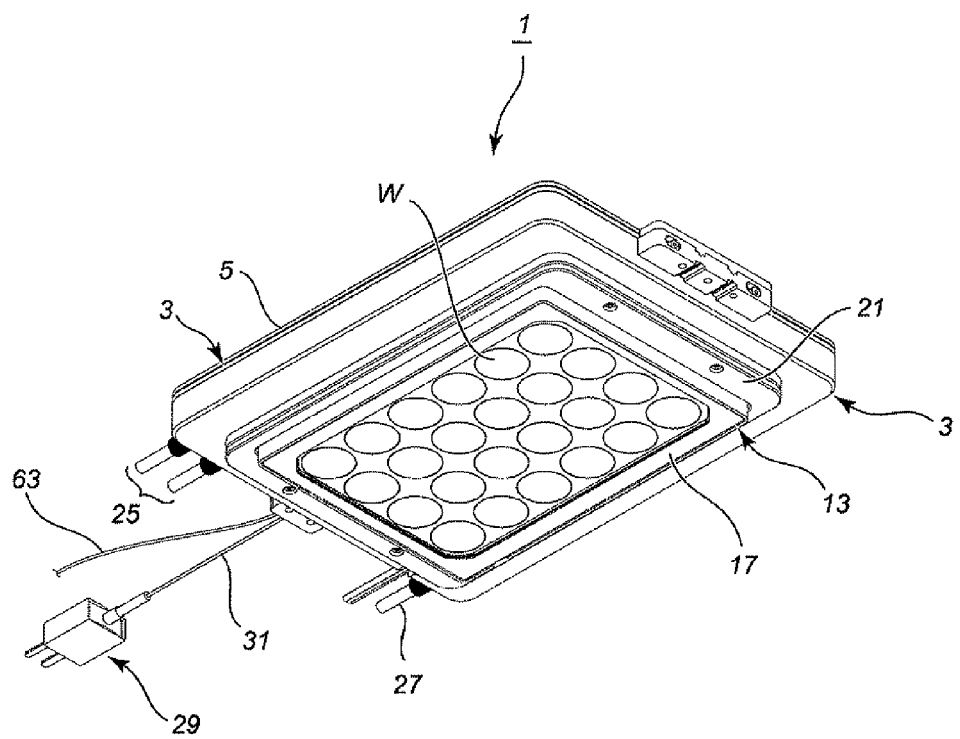
FIG. 3 is a perspective view of the FIG. 1 culture apparatus from the lower side.

Referring to FIG. 1, reference numeral 5 is added to a body portion of the unit 3. The body portion 5 has an upper opening 7 and a lower opening 9. The lower opening 9 has an inward flange 11 inwardly extending from the side portion, whereby it is smaller than the upper opening.

A substantially rectangular frame shaped adaptor 13 is fixedly fit, along its side surfaces, to the inner edges of the lower opening 9. The adaptor 13 has an inner flange 17 extending inwardly from the lower opening 15. Retaining springs 19 are removably connected at their base to four portions of the upper end surface of the adaptor 13. The adaptor 13 is to be used for a well plate W, and when the well plate W is fit to the adaptor 13, the well plate W can be retained therein stationary by means of spring force of the retaining springs 19.

The lower end surface of the adaptor 13 protrudes downwardly from the lower surface of the housing unit 3, to make a stepped portion 21.

The space defined by the inner side surface of the body portion 5, the outer side surface of the adaptor 13 and the inward flange 11 is adapted to be served as a water tank 23.

A pair of water supplying tubes 25 and a gas supplying tube 27 is adapted to be attached to the body portion 5. The tips of the water supplying tubes 25 are extended into the water tank 23, and the tip of the gas supplying tube 27 are extended into the water tank 23 and reaches to the bottom surface thereof.

There is prepared a temperature detecting means 29 having a thin-wired thermocouple-type detector 31. The housing unit 3 has, provided therewith, a detector holder 33 for guiding the detector 31. The detector holder 33 is positioned between the water supplying tubes 25 and the gas supplying tube 27. As can be seen from FIG. 5, the holder 33 includes a base block 35 and the retainer block 43. The base block 35 of the holder 33 is secured onto the outer side surface of the body portion 5. The base block 35 is provided with a pair of threaded holes 37 and a shallow groove 39 for passing the detector 31 there through. Further, a groove 41 is provided on the upper surface of the body portion 5 so as to align the groove 39 for guiding the detector 31 within the body portion 5 of the housing unit 3.

The retainer block 43 is also provided with a pair of holes 45 which will correspond to the holes 37 of the base block 35.

The detector 31 is passed through the groove 39 of the base block 35 and the groove 41 of the body portion 5, and the retainer block 43 is placed on the base block 35 so as to squeeze the detector 31 between a protrusion protruding from the lower surface of the retainer block 43 and the grooves 39, 41, and then the base block 35 and the retainer block 43 are secured by tightening the nuts 47. Thus, the detector 31 is secured to the body portion 5 with placing the tip thereof into the body portion 5. As can be seen from the above, the length of the detector 31 to be introduced within the body portion 5 can be adjusted so as to be enough that the tip of the detector 31 reaches a predetermined well w in the well plate W and is steeped therein.

The body portion 5 is also provided with a holder 51 for connecting a pair of perfusion hoses so that the culture apparatus 1 can be adjusted for perfusion culture.

The culture apparatus 1 is also provided with a lid 53 for closing the upper opening 7 of the housing unit 3.

Figure 4:
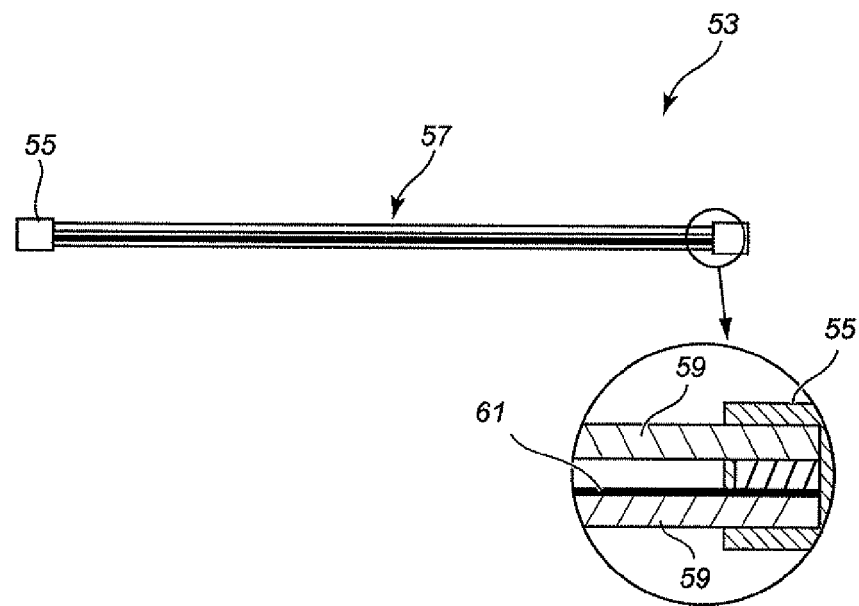
FIG. 4 is a cross-sectional view illustrating the lid of the FIG. 1 culture apparatus.
Figure 5:
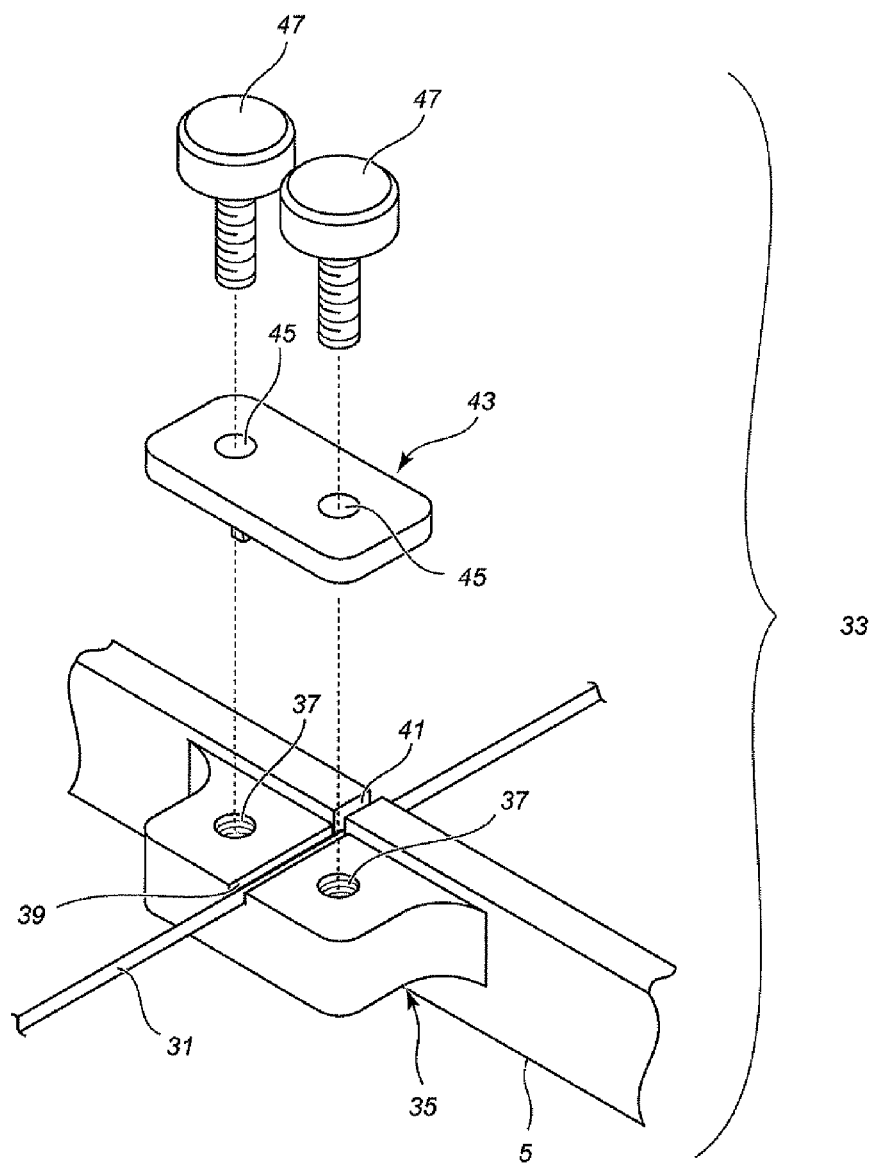
FIG. 5 is an enlarged perspective view illustrating part of the housing unit to which a detector holder for guiding and securing the detector of the temperature control means of the culture apparatus for microscope viewing.

As can be seen from FIG. 4, the lid 53 has a substantially rectangular shape. The lid 53 includes a frame 55 supporting a light permeable portion 57. The light permeable portion 57 is formed by a pair of juxtaposed transparent glass plates 59, 59 spaced with each other. On the upper surface of the lower glass plate 59 is formed a transparent conductive film 61. The transparent conductive film 61 is adapted to be served as a heater by providing electric energy thereto through the electric cord 63. The air layer formed between the glass plates 59, 59 is expected to be served as an insulation layer.

The cord 63 and the temperature detecting means 29 are both connected to the controller 65. The controller 65 is adapted to supply the electric energy to the transparent conductive film 61 by means of feedback control system on the basis of information from the detecting means 29 and a predetermined target temperature.

Although the well plate W to be installed in the adaptor 13 can be the one with or without lid, the well plate W of this embodiment is that with a lid 67. In this connection, the lid 67 is provided with a means for introducing the tip of the detector 31 of the temperature detecting means 29 into the predetermined well w.

Figure 6:
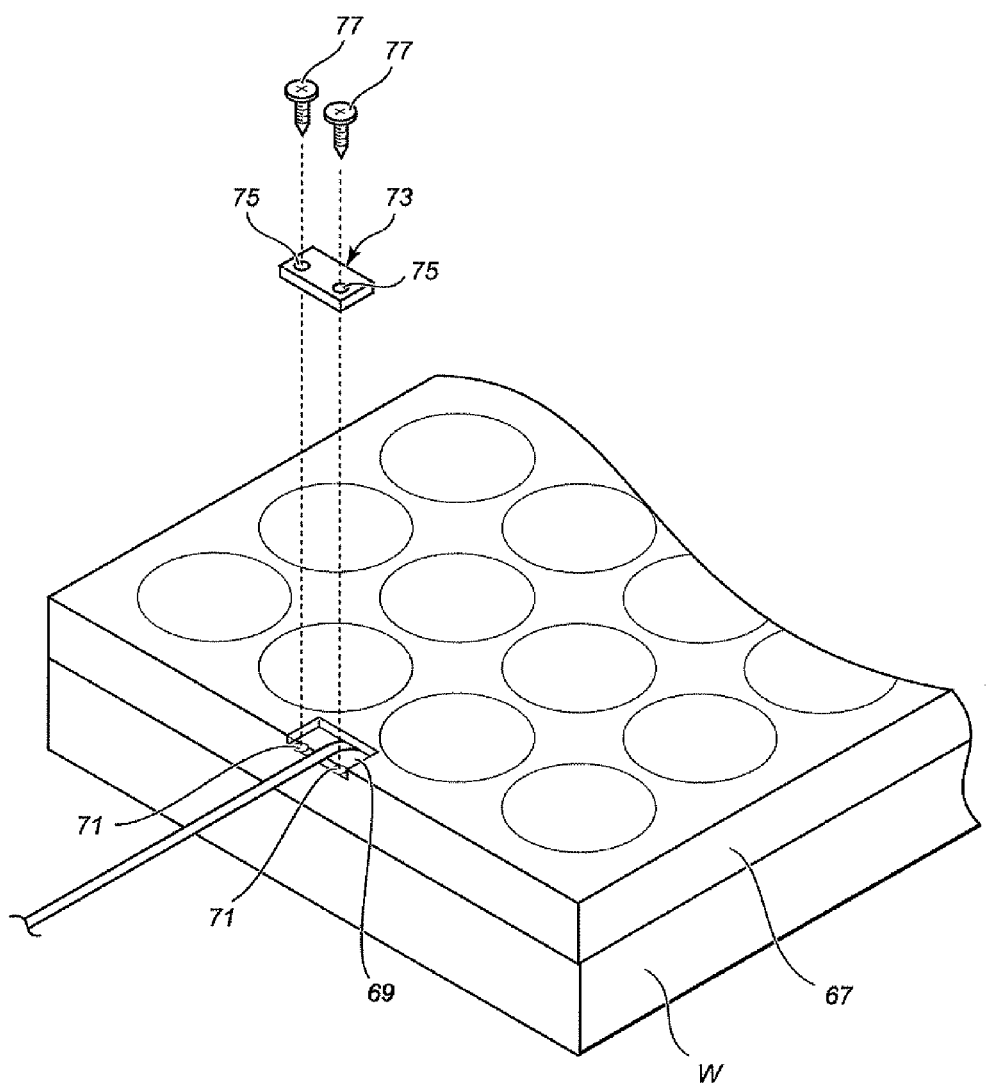
FIG. 6 is an enlarged perspective view illustrating the side of the container relating to the temperature control means of the FIG. 1 culture apparatus.
Figure 7:
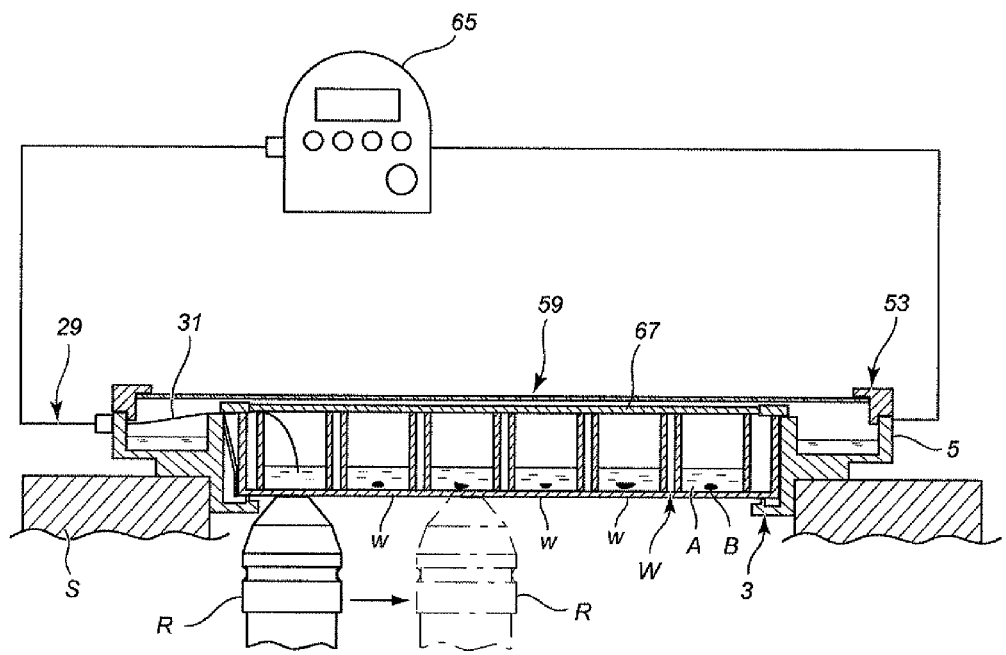
FIG. 7 is a cross-sectional view illustrating the behavior of the objective lens when used in the FIG. 1 culture apparatus.
Figure 8:
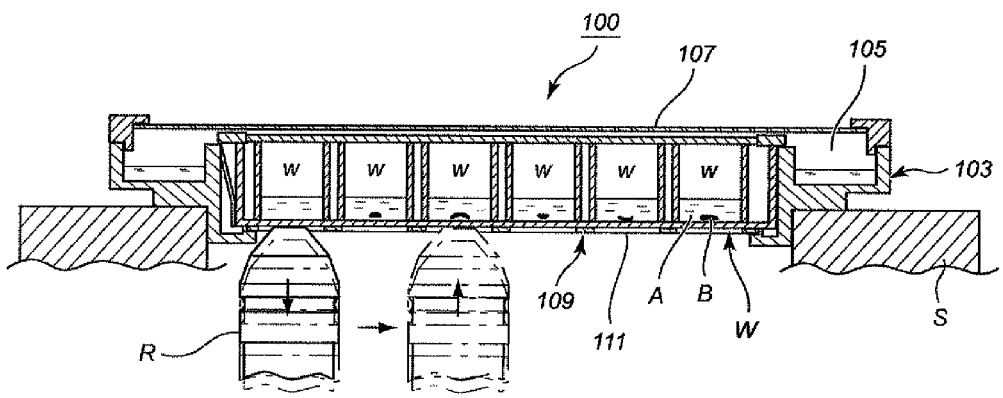
FIG. 8 is a cross-sectional view illustrating the behavior of the objective lens when used in a prior art culture apparatus.

The lid 67 is of transparent glass plate for suppressing fluorescence effect, and makes a box-shape. The lid 67 is adapted to mate with the stepped portion formed around the rim of the upper opening of the well plate W and fit thereinto to close the well plate W, as shown in FIG. 6. A small rectangular cutout is formed through the lid 67 along the side nearest to the holder 33. Thus exposed upper surface of the rim of the side wall of the well plate W is provide with a pair of threaded holes 71, 71 and a shallow groove (not shown) disposed between holes.

There is provided for securing the detector 31 to the well plate, a retainer plate 73 which be fit into the rectangular cutout 69. The retainer plate 73 has a pair of threaded holes 75, 75 corresponding to the holes 71, 71.

In order to secure the detector 31 to the well plate W, the detector 31 is passed through the groove, the retainer plate 73 is fit to the cutout 69 and then set screws 77, 77 are fastened through the threaded holes 75, 75 and 71, 71.

The detector 31 may be bent so that after the detector 31 is extended within the well plate W over a predetermined well w, the detector 31 can be bent to descend the tip thereof in the vicinity of the bottom surface of the well w.

The method for using the culture apparatus 1 for microscope viewing will now be described.

A dummy well plate W (which has been closed by the lid 67) is set within the adaptor 13, which has been installed preliminary to the body portion 5 of the housing unit 3, and the housing unit 3 is closed by the lid 53 to make a closed culturing space. Then $CO_2$ gas is supplied through the gas supplying tube 27, water is also supplied to the water tank 23 through the water supplying tube 25, and electric current is supplied to the transparent conductive film 61 of the transparent sheet top heater through the cords 63 to heat the atmosphere within the housing unit 3. Although not shown in the drawings, the bottom surface of the water tank 23 is also provided with a heater for evaporating the water contained within the water tank 23 to attain predetermined humidity within the closed culturing space. As can be seen, the gas supplying tube 27, the water supplying tube 25, and the heaters all fall within conditions under control of the controller 65 to provide the predetermined culturing condition.

The housing unit 3 of thus obtained culturing space is set on the stage S of the microscope. The stepped portion 21 of the body portion 5 of the housing unit 3 is adapted to hook on the edge of the opening provided through the stage S of the microscope.

On the other hand, a actual well plate W for microscope viewing is prepared. In one well w is filled the culture solution A, which is positioned along a side nearest to the holder 33. The one well is that exclusive for detecting the temperature within the wall plate, and filled only with the culture solution A. Within the other wells w are filled the culture solution A with the specimen B. The tip of the detector 31 of the temperature detecting means 29 exposed by removing protective sheath there around is then steep into the exclusive well w down to the bottom thereof for immersing into the culture solution A. Then, the upper opening of the well plate W is closed by the lid 67 and the detector 31 is secured thereto through the above-described means.

Upon completion of a preliminary run using the dummy well plate W for the predetermined period, the lid 53 is displaced, the dummy well plate W is removed from the housing unit 3, the actual well plate W is set therein, the detector 31 of the temperature detecting means 29 is fixed by means of the detector holder 33, and the housing unit 3 is again closed by the lid 53.

Since the culture solutions A with the specimens B within the wells w of the well plate W are kept in the predetermined humidity and temperature suitable being suitable for culturing, observation is possible for the specimens B.

Observation of the specimens B contained within a plurality of wells w may be carried out parallelly by shifting the stage S of the microscope.

The bottom surface portions of the well plate corresponding to the wells w are bared, and the spaces between wells w are also bared. In other words, the bottom surface of the well plate W defines flush surface which allows the stage S of the microscope to be shifted in the X-Y direction while keeping the objective lens R in the position nearest to the well w for making observation.

Since the distance between the transparent sheet top heater and any one of the wells w is kept constant, the culturing solution A and the specimen B contained in every wells w are heated equally.

The top heater is adapted to be energized on the basis of the information of the temperature of the culturing solution A detected directly through the detector 31 immersed within the culturing solution A, slight variation of the temperature is followed sequentially. In this connection, the temperature of the culturing solution A and the specimen B contained therein are be maintained always in the target temperature in high precision.

It is to be appreciated that the present invention has been described hereinabove with reference to certain embodiment of the invention but that various additions, deletions, alterations and modifications may be made thereto without departing from the intended sprit and scope of the invention.

For example, containers such as well plate are not limited to ones dedicated for the culture apparatus 1, and separately sold container may be used. However, if it is intended to close the container, it is recommended to use the lid as described above for make it easier to introduce the detector 31 of the temperature detecting means 29.

The container cannot be limited to well plate and one or more dishes can be utilized instead therefor. If two dishes are used, the one is dedicated for detecting the temperature within the dishes.

One dish or well is used only for detecting temperature, since the detector 31 may prevent observation and bring contaminants. Unless you mind such risks, the one dish or well may be used for detecting temperature as well as for observation.

INDUSTRIAL APPLICABILITY

The culture apparatus for microscope viewing in accordance with an embodiment of the present invention can be used as an accessory of the microscope.

EXPLANATION FOR REFERENCE NUMERAL

1 . . . culture apparatus 3 . . . housing unit 5 . . . body portion 7 . . . upper opening 9 . . . lower opening 11 . . . inward flange 13 . . . adaptor 15 . . . lower opening 17 . . . inner flange 19 . . . retaining spring 21 . . . water tank 25 . . . water supplying tubes 27 . . . gas supplying tube 29 . . . temperature detecting means 31 . . . detector 33 . . . detector holder 35 . . . base block 37 . . . threaded hole 39 . . . groove 41 . . . groove 43 . . . retainer block 45 . . . hole 47 . . . nut 49 . . . holder 51 . . . holder for perfusion culture 53 . . . lid 55 . . . frame 57 . . . light permeable portion 59 . . . transparent glass plates 61 . . . transparent conductive film 63 . . . electric cord 65 . . . controller 67 . . . lid (for well plate) 69 . . . rectangular cutout 71 . . . threaded hole 73 . . . retainer plate 75 . . . threaded hole 77 . . . screw W . . . well plate w . . . well A . . . culturing solution B . . . specimen S . . . stage of microscope R . . . objective lens

The invention claimed is:

1. A culture apparatus for microscope viewing enabling effective microscopic viewing a specimen placed on a stage of the microscope including a housing unit designed to accommodate a container holding a culture solution including the specimen therein, and a lid for closing an upper opening of the housing unit, with the housing unit having a lower opening of a size into which is removably fit a well plate and no heating plate narrowing the lower opening comprising:
- a transparent sheet top heater provided over a portion of the lid that corresponds to the viewing area; and
- a temperature detecting means in which a thin wire detector penetrates into the interior of the housing unit and further is immersed in the culture solution to measure the temperature of the culture solution supplied thereto directly;
- wherein the temperature of the transparent sheet top heater is controlled through a feedback method on the basis of the temperature information obtained from the temperature detecting means, and
- wherein no heating plate is placed in or below the lower opening.

2. The culture apparatus for microscope viewing according to claim 1 further comprising:
- a detector holder with a groove for introducing the detector of the temperature detecting means into the housing unit.

3. The culture apparatus for microscope viewing according to claim 2 further comprising:
- a container accommodated in the housing unit including a dedicated lid;
- wherein the detector of the temperature detecting means is adapted to be inserted into the container through a detector holder with a groove provided on the container.

4. The culture apparatus for microscope viewing according to claim 3 wherein:
- the container has a plurality of sections or is composed of a plurality of smaller containers,
- the detector of the temperature detecting means being introduced into one of the sections or one of the smaller containers to detect the temperature thereof, and the remaining sections or smaller containers being used for the microscopy of the specimen.

5. The culture apparatus for microscope viewing according to claim 3 wherein:
- the dedicated lid for the container is made of a transparent glass material.

6. The culture apparatus for microscope viewing according to claim 5 wherein:
- the container has a plurality of sections or is composed of a plurality of smaller containers,
- the detector of the temperature detecting means being introduced into one of the sections or one of the smaller containers to detect the temperature thereof, and the remaining sections or smaller containers being used for the microscopy of the specimen.

7. A method for using the culture apparatus for microscope viewing according to claim 5, comprising:
- accommodating the container having a plurality of sections or a plurality of smaller containers within the housing unit,
- introducing the detector of the temperature detecting means into one of the sections or one of the smaller containers to detect the temperature thereof, and
- using the remaining sections or smaller containers for the microscopy of the specimen.

8. A method for using the culture apparatus for microscope viewing according to claim 3, comprising:
- accommodating the container having a plurality of sections or a plurality of smaller containers within the housing unit,
- introducing the detector of the temperature detecting means into one of the sections or one of the smaller containers to detect the temperature thereof, and
- using the remaining sections or smaller containers for the microscopy of the specimen.

9. The culture apparatus for microscope viewing according to claim 2 wherein:
- a container having a plurality of sections or a plurality of smaller containers is accommodated within the housing unit,
- the detector of the temperature detecting means being introduced into one of the sections or one of the smaller containers to detect the temperature thereof, and the remaining sections or smaller containers being used for the microscopy of the specimen.

10. A method for using the culture apparatus for microscope viewing according to claim 2, comprising:
- accommodating a container having a plurality of sections or a plurality of smaller containers within the housing unit,
- introducing the detector of the temperature detecting means into one of the sections or one of the smaller containers to detect the temperature thereof, and
- using the remaining sections or smaller containers for the microscopy of the specimen.

11. The culture apparatus for microscope viewing according to claim 1 further comprising:
- a container accommodated in the housing unit including a dedicated lid;
- wherein the detector of the temperature detecting means is adapted to be inserted into the container through a detector holder with a groove provided on the container.

12. The culture apparatus for microscope viewing according to claim 11 wherein:
- the dedicated lid for the container is made of a transparent glass material.

13. The culture apparatus for microscope viewing according to claim 12 wherein:
- the container has a plurality of sections or is composed of a plurality of smaller containers,
- the detector of the temperature detecting means being introduced into one of the sections or one of the smaller containers to detect the temperature thereof, and the remaining sections or smaller containers being used for the microscopy of the specimen.

14. A method for using the culture apparatus for microscope viewing according to claim 12, comprising:
- accommodating the container having a plurality of sections or a plurality of smaller containers within the housing unit,
- introducing the detector of the temperature detecting means into one of the sections or one of the smaller containers to detect the temperature thereof, and
- using the remaining sections or smaller containers for the microscopy of the specimen.

15. The culture apparatus for microscope viewing according to claim 11 wherein:
- the container has a plurality of sections or is composed of a plurality of smaller containers,
- the detector of the temperature detecting means being introduced into one of the sections or one of the smaller containers to detect the temperature thereof, and the remaining sections or smaller containers being used for the microscopy of the specimen.

16. A method for using the culture apparatus for microscope viewing according to claim 11, comprising:
- accommodating the container having a plurality of sections or a plurality of smaller containers within the housing unit, introducing the detector of the temperature detecting means into one of the sections or one of the smaller containers to detect the temperature thereof, and using the remaining sections or smaller containers for the microscopy of the specimen.

17. The culture apparatus for microscope viewing according to claim 1 wherein:

a container having a plurality of sections or a plurality of smaller containers is accommodated within the housing unit, the detector of the temperature detecting means being introduced into one of the sections or one of the smaller containers to detect the temperature thereof, and the remaining sections or smaller containers being used for the microscopy of the specimen.

18. A method for using the culture apparatus for microscope viewing according to claim 1, comprising:

accommodating a container having a plurality of sections or a plurality of smaller containers within the housing unit, introducing the detector of the temperature detecting means into one of the sections or one of the smaller containers to detect the temperature thereof, and using the remaining sections or smaller containers for the microscopy of the specimen.

* * * * *